United States Patent

Coffen et al.

[11] Patent Number: 4,558,140
[45] Date of Patent: Dec. 10, 1985

[54] CYCLOPENTA[B]FURAN-2-ONES

[75] Inventors: David L. Coffen, Glen Ridge; George W. Holland, North Caldwell; Perry Rosen, North Caldwell; Frederick Wong, Glen Ridge, all of N.J.

[73] Assignee: Hoffmann-La Roche Inc., Nutley, N.J.

[21] Appl. No.: 586,586

[22] Filed: Mar. 6, 1984

[51] Int. Cl.$^4$ .................................. C07D 307/93
[52] U.S. Cl. .................. 549/312; 562/503; 549/311; 549/465
[58] Field of Search ........................ 549/312

[56] References Cited

U.S. PATENT DOCUMENTS 4,044,005 8/1977 Kienzle et al. .................. 549/312

OTHER PUBLICATIONS

Overman et al., Tet. Letters, 4, 321-324, (1979).
Vasil'eva et al., J. Gen. Chem. USSR 52, 2346–47, (1982).
Grieco et al., J. Am. Chem. Soc. 102, 7587–88, (1980).
Grieco et al., J. Org. Chem. 46, 5005–07, (1981).

*Primary Examiner*—Jane T. Fan
*Attorney, Agent, or Firm*—Jon S. Saxe; Bernard S. Leon; George W. Johnston

[57] ABSTRACT

New optically active intermediates and processes thereto are provided for use in synthesizing therapeutically active prostaglandins of the formula:

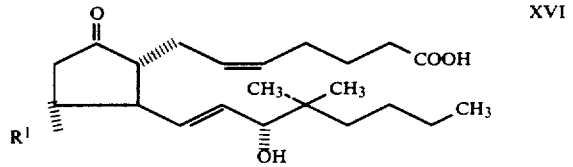

wherein $R^1$ is hydrogen or lower alkyl; from a compound of the formula:

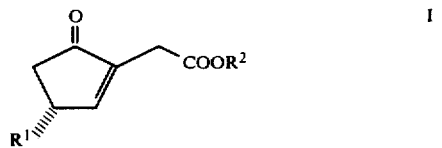

wherein $R^1$ is as above and $R^2$ is hydrogen or a carboxy blocking group convertible to an acid by hydrolysis.

9 Claims, No Drawings

CYCLOPENTA[B]FURAN-2-ONES

BACKGROUND OF THE INVENTION

1. Field of the Invention

This invention concerns a novel process for preparing prostaglandins and novel prostaglandin intermediates.

2. Description

Prostaglandins are well known therapeutic agents which have been used as cardiovascular agents, as agents to induce labor or terminate pregnancy in pregnant females, as antisecretory agents for preventing hyperacidity and as anti-ulcerogenic agents.

Processes for the preparation and the administration of therapeutically effective prostaglandins are disclosed in U.S. Pat. Nos. 4,052,446; 4,190,587; 4,154,963; 4,390,718 and 4,227,019.

SUMMARY OF THE INVENTION

New optically active intermediates and processes thereto are provided for use in synthesizing therapeutically active prostaglandins of the formula:

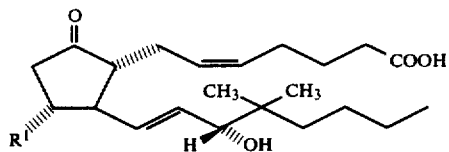

XVI wherein $R^1$ is hydrogen or lower alkyl from a compound of the formula:

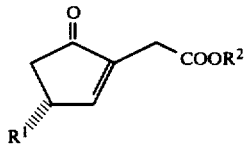

I wherein $R^1$ is as above and $R^2$ is hydrogen or a carboxy blocking group convertible to an acid by hydrolysis.

The inventive processes for producing Compound XVI from Compound I are set forth in the scheme below. While Compounds I through XX are preferably the optical active enantiomers, the processes are also applicable to their racemates.

In a preferred aspect of the invention, only the optically active enantiomers are utilized in the processes and advantageously produce the optically active enantiomer Compound XVI.

DETAILED DESCRIPTION OF THE INVENTION

The present invention relates to new optically active and racemic intermediates for prostaglandins and to new processes for producing prostaglandins of formula:

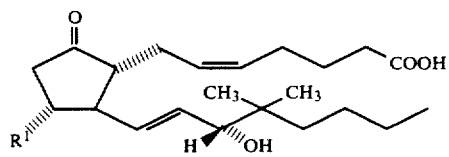

XVI wherein $R^1$ is hydrogen or lower alkyl, from a compound of formula:

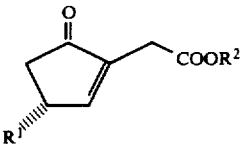

I wherein $R^1$ is as above and $R^2$ is hydrogen or a carboxy blocking group convertible to an acid by hydrolysis.

As used throughout this application, the term "lower alkyl" includes both straight chain and branched chain alkyl groups having from 1 to 7 carbon atoms, such as methyl, ethyl and propyl, preferably methyl.

As used herein, the term "lower alkoxy" comprehends groups having from 1 to 7 carbon atoms such as methoxy and ethoxy.

As used herein the term "lower alkanol" comprehends alcohols, wherein the lower alkyl moiety is as defined above.

As also used herein, the term "lower alkanoic acid" comprehends an alkanoic acid of 1 to 7 carbon atoms such as formic acid and acetic acid.

As further used herein, the term "halogen" or "halide", unless otherwise stated, comprehends fluorine, chlorine, bromine and iodine. Chlorine is preferred.

As also used herein, the term "aryl" signifies mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be substituted with one or more of the aforementioned groups. The preferred aryl groups are the substituted and unsubstituted mononuclear aryl groups, particularly phenyl.

The term "aryl lower alkyl" comprehends groups wherein aryl and lowr alkyl are as defined above, particularly benzyl.

The term "aryl lower alkanoic acid" comprehends acids wherein "aryl" and "lower alkanoic acid" are as defined above, particularly benzoic acid.

As still further used herein, the term "carboxy blocking group convertible to an acid by hydrolysis" comprehends any conventional organic acid protecting group which can be hydrolyzed to yield the acid. Exemplary protecting groups useful for this purpose are lower alkyl, (particularly methyl and ethyl), aryl, (particularly phenyl) and aryl lower alkyl, (particularly benzyl).

As used herein, the term "hydrolyzable ether protecting group" designates any conventional ether protecting group, which when the ether is hydrolyzed, will yield the hydroxy group. A preferred hydrolyzable ether protecting group is tetrahydropyranyl. Other suitable groups are arylmethyl such as benzyl, benzyhydryl, or trityl; or lower alkoxy, lower alkyl, (for example, methoxymethyl, 2-methoxy-2-propyl), or allyl; or a trialkyl silyl such as trimethyl silyl or dimethyltertbutyl silyl.

As used herein in term "acyl" means a radical derived from a carboxylic acid and has the formula:

wherein R is hydrogen, alkyl or aryl.

Preferably, R is hydrogen, lower alkyl or phenyl. Typical acyl groups are formyl, acetyl, propionyl, butyryl, benzoyl and the like. Most preferably, R is methyl.

The term "acid halide" denotes a compound of the formula

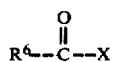

wherein $R^6$ is hydrogen, lower alkyl, halo lower alkyl, lower alkoxy, halo lower alkoxy, aryl, aralkyl, aryloxy or aryl lower alkoxy and X is halogen.

The term "acid anhydride" denotes a compound of the formula

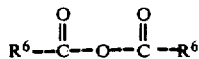

wherein $R^6$ is as defined above.

The term "alkali metal" includes all of the alkali metals such as lithium, sodium, potassium and the like.

The term "alkaline earth metal" includes all of the conventional alkaline earth metals such as calcium, magnesium and the like.

In the pictorial representation of the compounds given throughout this application, a thickened tapered line (◂) indicates a substituent which is in the beta-orientation (above the plane of the molecule), a dotted line (ııııı) indicates a substituent which is in the alpha-orientation (below the plane of the molecule) and a wavy line (∼) indicates a substituent which is in either the alpha- or beta-orientation or mixtures of these isomers. It is to be understood that the pictorial representations of optically active compounds given throughout the specification are set forth for convenience and are to be construed as inclusive of their racemates and are not to be construed as limited to the particular form shown.

According to the invention, compound XVI can be made from Compound I by the following reaction scheme:

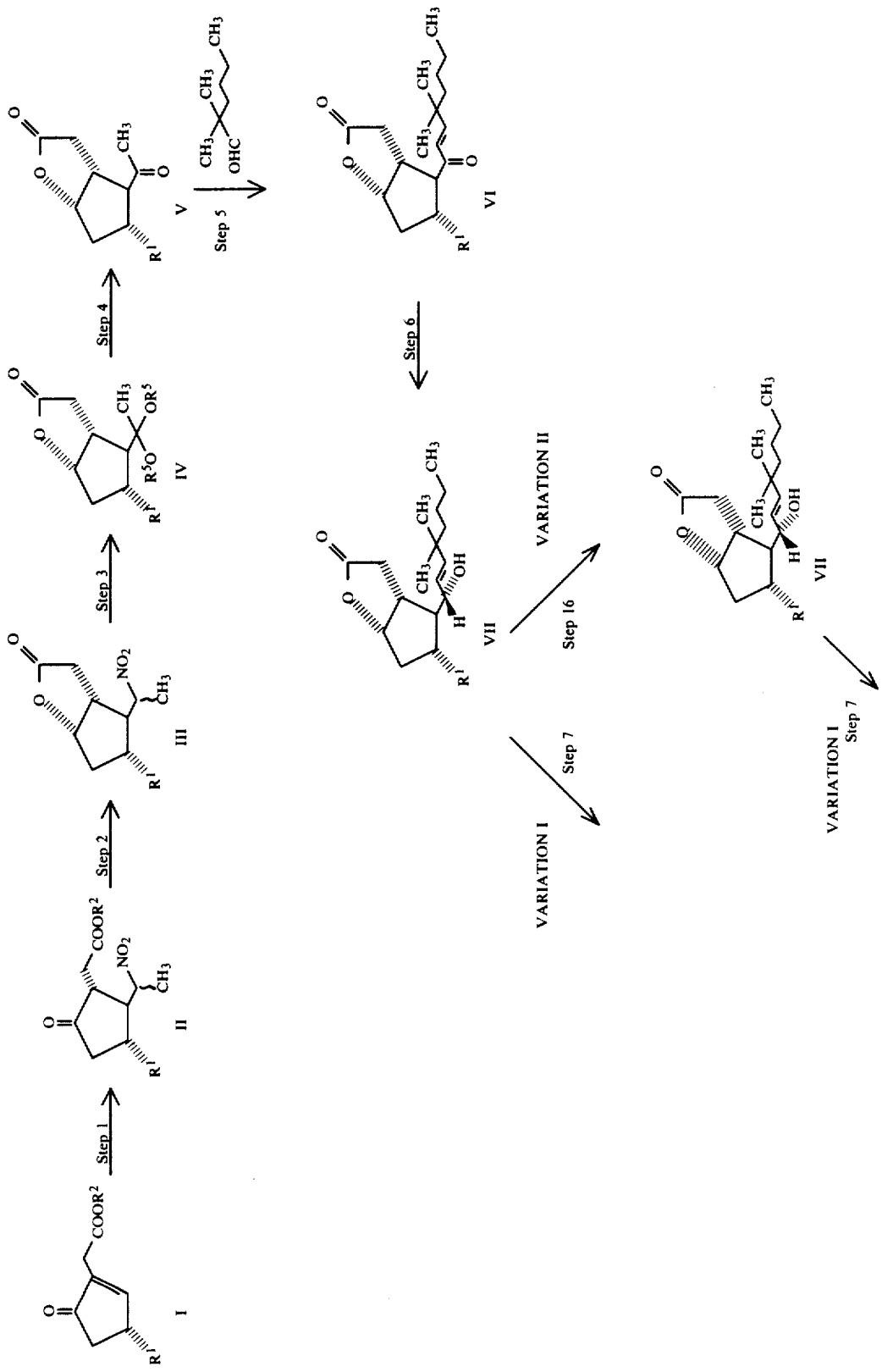

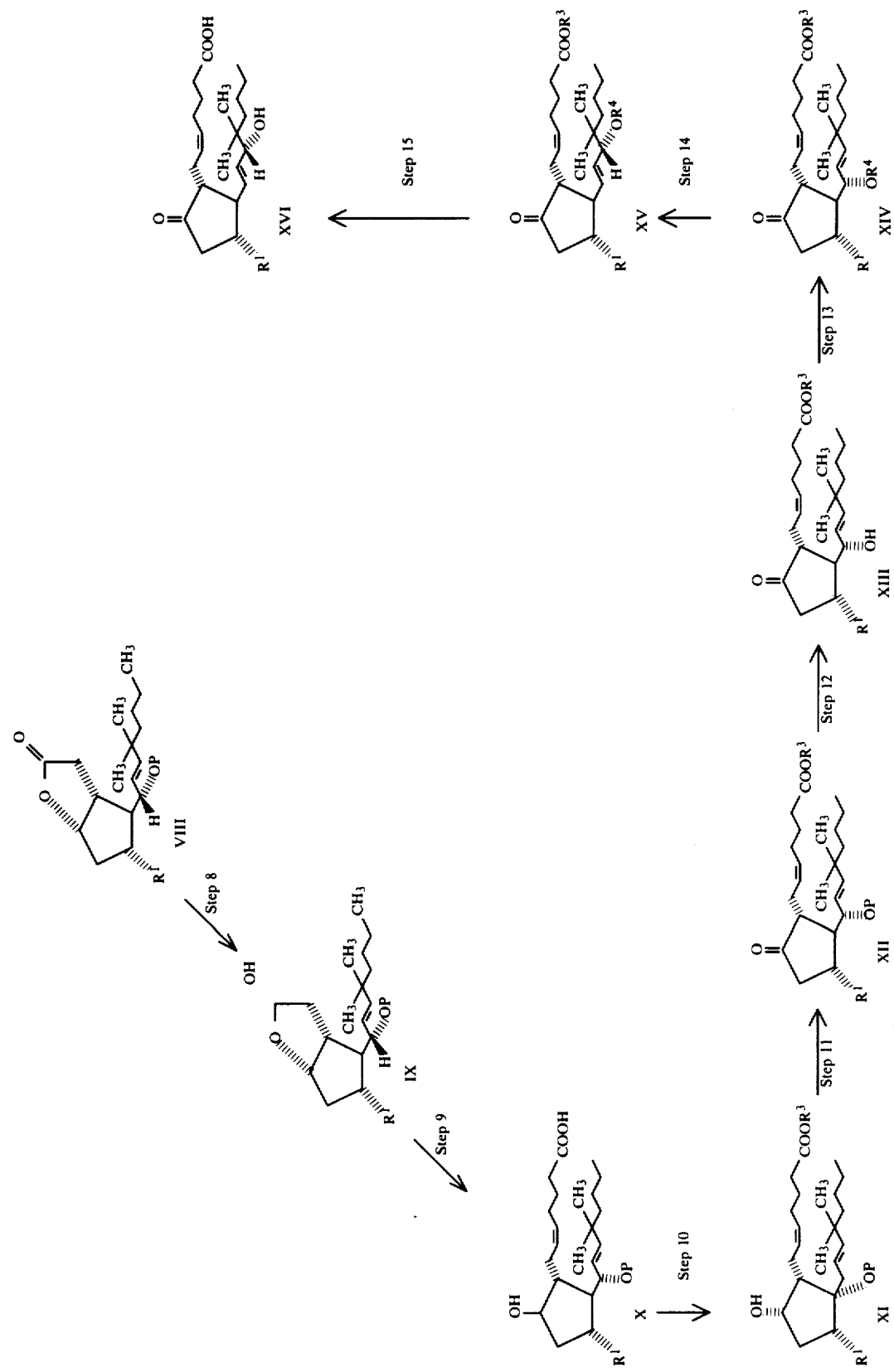

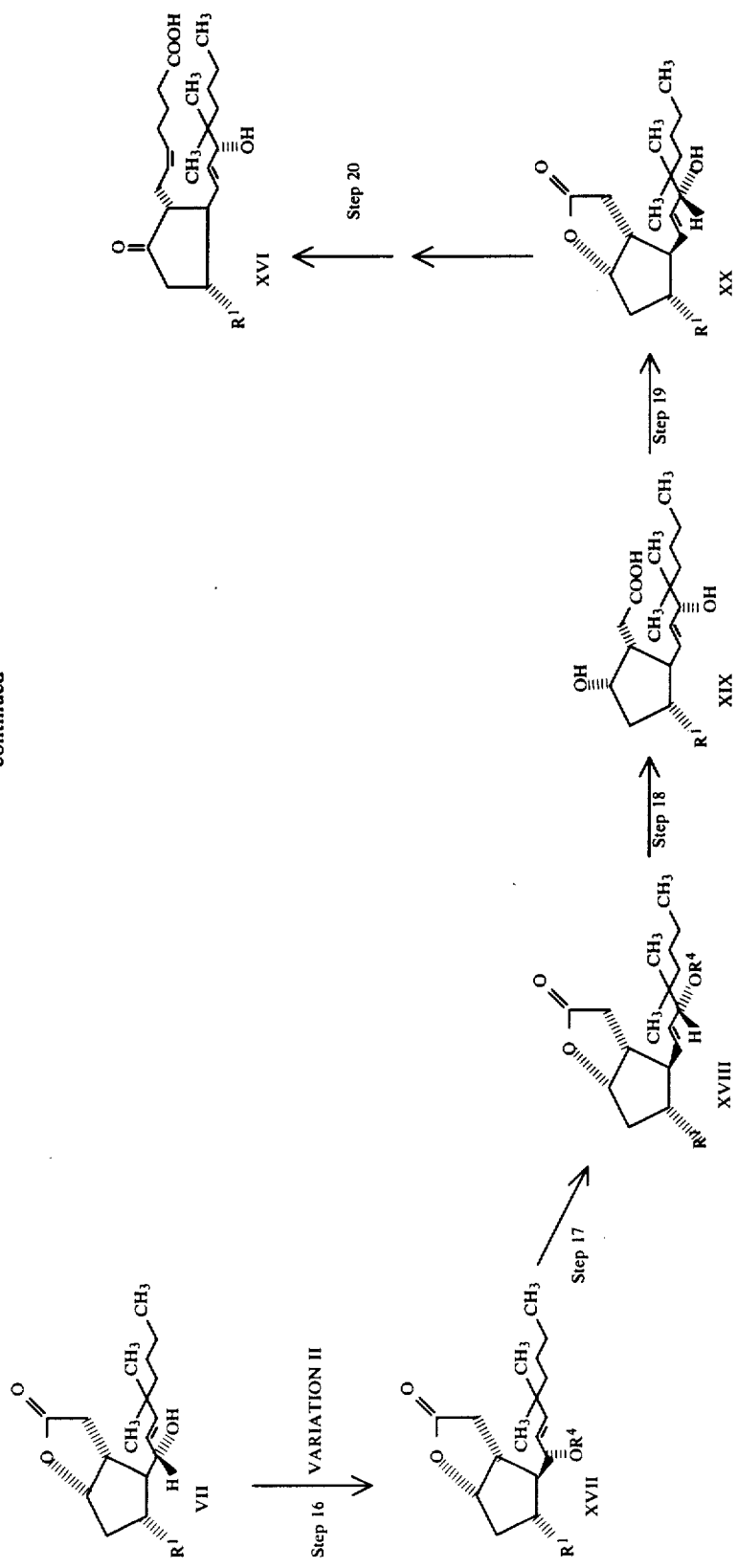

wherein
- $R^1$ is hydrogen or lower alkyl, (preferably methyl);
- $R^2$ is hydrogen or a carboxy blocking group convertible to an acid by hydrolysis;
- $R^3$ is a carboxy blocking group convertible to an acid;
- $R^4$ is acyl;
- $R^5$ individually is lower alkyl or taken together both $R^5$s can be lower alkylidene thereby forming a ring with the adjacent carbon atom; and
- P is a hydrolyzable ether protecting group.

In the above scheme the reaction processes are designated as steps 1-20, while the formulae representing the starting materials, intermediates and end products are designated by Roman numerals I-XX.

The term "room temperature" as used in describing the steps of the process means from about 20° to about 25° C. Throughout the application whenever a temperature is below 0° C., it is written with a negative sign and is enclosed is parentheses, for example (−78)°C. Pressure is not critical for any of the steps of the process and unless otherwise stated the reaction step is preferably carried out at atmospheric pressure.

In accordance with the above reaction scheme, the process of the present invention provides the compound of formula XVI from the compound of formula I.

In Step 1 the starting materials, Compound I and nitroethane, react via a Michael conjugate addition reaction to form Compound II.

Compound I is reacted with nitroethane and a suitable base. Preferably only catalytic amounts of the base are employed. A suitable base to catalyze the reaction is any alkali metal alkoxide or hydroxide base such as sodium methoxide and sodium ethoxide. A preferred base is trimethylbenzylammonium hydroxide.

Any conventional organic solvent may also be used in Step 1, such as a hydrocarbon or alcohol solvent provided it does not react with the base and does not compete with the desired reaction forming Compound II. Preferred solvents are toluene, ethanol and an excess of nitroethane.

Temperature is not critical for the reaction of Step 1 but it is preferably carried out at temperatures from about 0° C. to about the reflux temperature of the solvent, with a more preferred temperature being about 50° C.

The reaction product, the compound of formula II, as well as the other reaction products formed in the steps of this process may be isolated, if desired, by conventional methods well known in the art such as distillation, crystallization, and chromatographic methods such as column, or high pressure liquid chromatography and the like. In some steps of this process its convenient to proceed to the next step without isolating and purifying the formed product.

In Step 2 Compound II is reduced and a spontaneous lactonization ensues. Any conventional reducing agent which selectively reduces a ketone but does not reduce an ester or nitro group may be used. Examples of such reducing agents are the alkaline or alkali earth metal borohydrides or the aluminum alkoxides of secondary alcohols as well as a reagent prepared from diisobutyl aluminium hydride and butylated hydroxy toluene (DIBAL-BHT). Preferred borohydride reagents are sodium borohydride, potassium borohydride, lithium borohydride and especially potassium or lithium tris-secondary butylborohydride. A preferred aluminium alkoxide of a secondary alcohol is aluminium isopropoxide.

The solvent in Step 2 can be critical depending upon the reducing agent employed. For the alkaline or alkali earth borohydride reagents suitable solvents include alcohols especially methanol or ethanol. When the reducing agent is potassium or lithium tris-secondary butylborohydride, ether solvents are used, for example tetrahydrofuran or diethylether. When the reducing agent is an aluminium alkoxide of a secondary alcohol the preferred solvent is the corresponding alcohol, for example, isopropyl alcohol for aluminium isopropoxide.

The reaction of Step 2 can take place at temperatures ranging from about (−78)°C. to about the reflux temperature of the solvent. The preferred temperature when the reducing agent is aluminium isopropoxide is the reflux temperature of the solvent. The preferred temperature when the reducing agent is sodium borohydride is 0° C., and the preferred temperature the reaction when the reducing agent potassium or lithium tris-secondary butyl borohydride is (−78)°C.

Step 3 is a reaction of the type known as the Nef reaction, wherein the nitroalkane of formula III is converted to the ketal of formula IV.

Step 3 can be described as two substeps (a) and (b).

In substep (a) Compound III is treated with a base to convert it to the nitronate form. The base may be any alkali metal hydroxide or alkali metal alkoxide, such as sodium hydroxide, lithium hydroxide, or potassium hydroxide. The reaction must take place in a solvent which may be a lower alkanol. A preferred base solvent combination is sodium hydroxide in methanol. The temperature at which the base is added to Compound III in substep (a) is generally from about (−20) to about 20° C. A preferred temperature for the preferred sodium hydroxide-methanol combination is about 0° C.

In substep (b) of step 3, a strong mineral acid in the same solvent as used for substep (a) is combined with the solution of nitronate. Suitable mineral acids include sulfuric acid, hydrochloric acid and phosphoric acid. The preferred mineral acid is sulfuric acid. Preferably the solvent used in substep (b) is the same solvent as that used in substep (a).

The temperature at which substep (b) occurs ranges from about (−50)° to about 0° C. The preferred temperature is from about (−25)°C. to about (−35)°C.

In step 4 water and any acid which forms a volatile ester are added to the mixture. The preferred acids are formic or acetic acid. The addition of this aqueous acid forms the methyl ketone compound of formula V, which, if necessary, can be purified by vacuum distillation. However the use of the crude material gives the best over all yield in the next step, Step 5.

Step 5 is an aldol condensation reaction wherein the reagent 2,2 dimethylhexanal is condensed with the reaction product of step 4, compound V.

The Step 5 condensation requires any conventional base used in aldol condensations. Suitable bases include alkali metal alkoxides or a strong organic base. Preferred bases are sodium methoxide, sodium ethoxide and potassium butoxide. The temperature range for the condensation is from about 0° C. to about the reflux temperature of the mixture. The preferred temperature range is from about room temperature to about 55° C.

Although not necessary, this aldol condensation may take place in any suitable solvent. Some suitable solvents are lower alkanols, ethers, dimethylformamide (DMF) and dimethylsulfoxide (DMSO). Preferred solvents are lower alkanols such as methanol, ethanol, tertiary butyl alcohol as well as tetrahydrofuran (THF) and dioxane.

In Step 6 the ketone function of compound VI is selectively reduced to form compound VII by conventional reduction techniques. Any conventional reducing agent which will selectively reduce the ketone in the presence of the ester and double bond may be used. Examples of such reagents are the alkaline or alkali earth metal borohydrides or the aluminum alkoxides of secondary alcohols as well as potassium or lithium tris-secondary butylborohydrides and DIBAL-BHT. Preferably potassium tris-secondary butylborohydride or sodium borohydride are the reducing agents.

In Step 6, suitable solvents include water, alcohols and water-alcohol mixtures. When the reducing agent is potassium or lithium tris-secondary butylborohydride the solvent must be an ether type solvent such as tetrahydrofuran (THF), dioxane or diethyl ether.

The temperature of the reaction Step 6 also depends upon the reducing agent employed and generally ranges from about (−78)°C. to about the reflux temperature of the solvent. For example, if the reducing agent is sodium borohydride, the preferred temperature is approximately 0° C.; if the reducing agent is aluminum isoproproxide, the preferred temperature is approximately 50° C.; and if the reducing agent is potassium tris-secondary butylborohydride, the preferred reaction temperature is approximately (−78)°C.

The following Steps 7 through 15 describe Variation I of applicants' inventive process for producing Compound XVI.

In Step 7 the compound of formula VII can be converted to a compound of the formula VIII by etherifying the free hydroxy group of Compound VII with a hydrolyzable ether protecting group. This etherification can be carried out by conventional etherification procedures. Among the preferred hydrolyzable ether groups are trimethylsilyl, 2-methoxy-2-propyl, and most preferably tetrahydropyranyl (THP).

In Step 8, the lactone group of Compound VIII is reduced to a lactol group by treatment with a reducing agent. In carrying out this reaction, any conventional reducing agent which will selectively reduce a lactone group to a lactol group can be utilized. Preferred reducing agents are the hydrides, particularly the aluminum hydrides such as lithium aluminum hydride, and the borohydrides such as lithium borohydride, with diisobutyl aluminum hydride being particularly preferred. This reaction, is best carried out at lower temperatures, with from about (−78)°C. to about 0° C., being preferred.

This reduction reaction can be carried out in the presence of an inert organic solvent. Any conventional, inert organic solvent can be utilized. Among the preferred solvents are toluene, dimethoxyethane (DME), diethyl ether, tetrahydrofuran (THF), and dioxane.

In Step 9, the compound of formula X is obtained from the compound of formula IX by reacting the compound of formula IX with phosphonium salts of the formula:

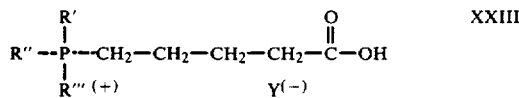

wherein R', R" and R"' are aryl or di(lower alkyl)amino groups and Y is halogen and a strong base capable of generating the corresponding ylide from the phosphonium salt. Among the preferred bases are lithium diisopropyl amide, sodium hydride, lithium hexamethyldisilazide, and potassium t-butoxide.

In accordance with this invention, it is found that the compound of formula IX will react with the ylide derived from such phosphonium salts to produce a compound of formula X in which the double bond at the 5-position of the acid-containing side chain is cis.

In Step 10 the compound of formula XI is obtained from the compound of formula X by esterification. Any conventional esterification method may be utilized. Of the conventional methods of esterification, those methods which leave the hydrolyzable ether protecting group intact are preferred. Among the preferred methods of esterification are treatment with diazomethane in an ether solvent and treatment with a mixture of methyl iodide and sodium bicarbonate in a polar solvent such as dimethylformamide or dimethylacetamide.

In Step 11 the compound of formula XII is obtained from the compound of formula XI by oxidation. Any conventional reagent known for effecting the oxidation of a secondary alcohol to a ketone, is suitable for the oxidation of the compound of formula XI to the compound of formula XII. Among the preferred reagents are chromium trioxide in a mixture of sulfuric acid and acetone (Jones' reagent), chromium trioxide in pyridine, oxalyl chloride in dimethylsulfoxide, and dimethylsulfoxide containing triethylamine and pyridine/sulfur trioxide complex.

In Step 12 the compound of formula XIII is obtained from the compound of formula XII by selective hydrolysis of the hydrolyzable ether protecting group, without simultaneously hydrolyzing the ester group. Any conventional method for accomplishing such selective hydrolysis may be employed. The preferred methods of carrying out this selective hydrolysis are to treat the compound of formula XII with weakly acidic reagents in the presence of lower alkanols, water and lower alkanol mixtures, or water and water soluble solvent mixtures. Examples of such water soluble solvents are ether, acetone, and tetrahydrofuran. A preferred method is to treat the compound of formula XII with pyridinium p-toluenesulfonate in methanol solution.

In Step 13 the compound of formula XIV is obtained from the compound of formula XIII by esterification with a suitable base solvent derivative of a lower alkanoic acid reagent. Suitable derivatives of lower alkanoic acids are the derived acid halides, such as acetyl chloride, and acid anhydrides such as acetic anhydride and formic-acetic mixed anhydride. A preferred method for esterification of the compound of formula XIII is acetylation by treatment with acetic anhydride in a solvent such as mixture of methylene chloride and pyridine containing a catalytic amount of 4-dimethylaminopyridine.

Step 14 is a catalytic allylic ester isomerization reaction wherein a divalent palladium compound is added as a catalyst to compound XIV. Examples of divalent palladium compounds which may be used as catalysts for Step 14 are bis-acetonitrile palladium (II) halide or bis-benzonitrile palladium (II) halide. The preferred catalyst is bis-acetonitrile palladium (II) chloride. Although there is no specific limit or the amount of divalent palladium catalyst which can be utilized, the preferred amount is up to about 10% by weight of the starting material, Compound XIV, with about 5 to about 8% being especially preferred. The solvent in which the reaction takes place is usually an ether solvent. For example, cyclic ethers such as tetrahydrofuran (THF) or dioxane or linear ethers such as 1,2-dimethoxyethane or diethyl ether, may be used, THF is the preferred solvent. It is preferred that the solvent be pure othewise the catalyst may be poisoned. It is also preferred to exclude oxygen from the reaction mixture. The temperature of the reaction ranges from about 23° C. to about 120° C. and is preferably about 55° to about 60° C.

The conversion of compound XIV to compound XV is not complete but goes to an equilibrium mixture of compounds XIV and XV. The desired compound XV can be isolated from this mixture by chromatography.

In Step 15, compound XV is converted to compound XVI by any conventional hydrolysis technique. Preferably the hydrolysis employs an alkali metal hydroxide reagent in a lower alkanol solvent to form the alkali metal salt of Compound XVI, which in turn is acidified by conventional methods. Most preferably the hydrolysis employs sodium hydroxide in methanol. The temperature of the Step 15 hydrolysis can range from 0° C. to the reflux temperature of the solvent.

The following Steps 16 through 20 describe Variation II of applicants' inventive process for producing Compound XVI.

In Step 16, compound VII is converted to compound XVII in a manner analagous to step 13 of the scheme (wherein compound XIII is converted to compound XIV), except that the product of Step 16, compound XVII, is a crystalline compound which is most conveniently isolated and purified by crystallization.

In step 17, the compound XVII is converted to the compound XVIII by an allylic ester isomerization reaction employing essentially the same method used in prior step 14 to convert compound XIV to compound XV. Although, again as in Step 14, there is no specific limit in the amount of divalent palladium catalyst which can be utilized, in the Step 17 isomerization it is preferred to use up to about 10% by weight based on the starting material, Compound XVII, and especially preferred to employ up to about 4%. The preferred temperature for the reaction is from about 0° C. to about 120° C. with the most preferred being from about 20° C. to 25° C.

More particularly, the catalytic compounds useful for Step 17 are conventional divalent palladium catalysts, for example, bis-acetonitrile palladium (II) halide and bis-benzonitrile palladium (II) halide. Bis-acetonitrile palladium (II) chloride is preferred. In Step 17 any conventional ether-type solvent is employed. The preferred solvents are cyclic ethers such as tetrahydrofuran [THF] or dioxane and linear ethers such as 1,2-dimethoxyethane or diethyl ether. The most preferred solvent is THF. Again as in step 14, it is preferred that the solvent be pure otherwise the catalyst may be poisoned and also preferred to exclude oxygen from the reaction. Similar to Step 14, Step 17 like also goes only to an equilibrium mixture of compounds XVII and XVIII.

While, it is possible to isolate compound XVIII by liquid chromatography after Step 17, it is preferred to employ the crude mixture of compounds XVII and XVIII in Step 18 and separate the desired isomer afterwards because the desired isomer will crystallize directly from the compound mixture produced from the Step 18 hydrolysis.

In Step 18, compound XVIII is hydrolyzed to form compound XIX by any conventional method of basic hydrolysis. Only basic hydrolysis reagents may be used, preferably alkali metal hydroxides and especially sodium hydroxide. The reaction may take place in a water and organic solvent, preferably water and toluene, so as to from the alkali metal salt of Compound XIX, which is then acidified to form Compound XIX. When the basic hydrolysis mixture is acidified, care must be taken to avoid lactonization. A preferred method of acidification is adding phosphoric acid at about 0° C. The desired compound XIX crystallizes from the crude mixture when this acidification method is employed.

In Step 19, compound XIX is converted to compound XX by any conventional method of cyclizing a lactone. Examples of preferred methods for effecting this lactonization are treatment with acetic acid or heating in toluene solution. This reaction is extremely facile.

In Step 20, compound XX can be converted to compound XVI via intermediate Compounds XXI, XXII, XXIV and XXV by steps analogous to those employed in U.S. Pat. Nos. 4,052,446 and 4,190,587.

More particularly, the compound of formula XX is first converted by etherification of the free hydroxy group to a compound of the formula:

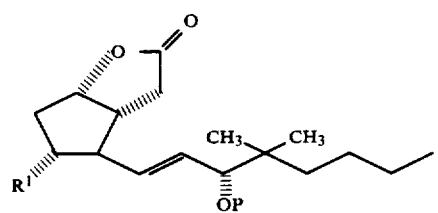

XXI wherein
$R^1$ is hydrogen or lower alkyl, and
P is a hydrolyzable ether protecting group.

The compound of formula XXI is the converted by partial reduction of the lactone group to a lactol group, to a compound of the formula:

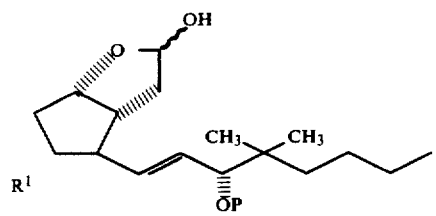

XXII wherein
$R^1$ is as above, and
P is as above.

The compound of formula XXII is then reacted via a Wittig reaction in the presence of a strong base with phosphonium salts of the formula XXII:

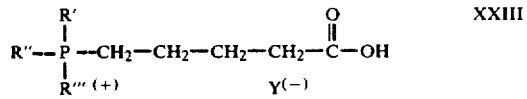

XXIII wherein R', R" and R"' are aryl or di(lower alkyl) amino groups and Y is halogen: to form an intermediate compound of the formula:

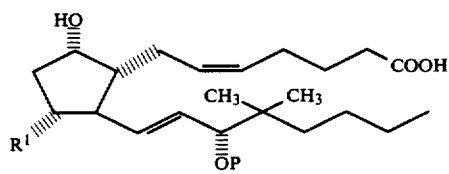

XXIV wherein
R¹ is as above and
P is as above.

The free hydroxy group of Compound XXIV is then oxidized to the ketone compound of formula:

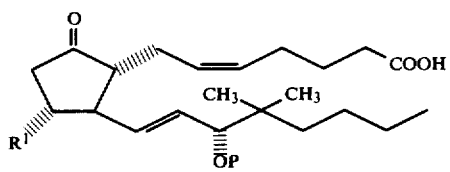

XXV wherein
R¹ is as above and
P is as above.

In the final step, the compound of formula XXV is converted to the compound of formula XVI by hydrolysis.

In accordance with the above procedures described in Steps 1-20, and U.S. Pat. Nos. 4,052,446 and 4,190,587 optically active Compound I is converted to optically active Compound XVI via two variations. When racemic Compound I is utilized as the starting material and the reaction scheme is followed, the racemate of Compound XVI results.

More particularly, racemic Compound I is reacted with nitroethane via a Michael conjugation addition reaction to form racemic Compound II. The ketone function of racemic Compound II is then reduced and spontaneously lactonizes to form racemic nitroalkane Compound III which is then converted to the racemic ketal Compound IV. Racemic Compound IV is converted to racemic ketone of Compound V by hydrolysis. Racemic Compound V is then condensed with 2,2 dimethylhexanal to form racemic ketone Compound VI which is then selectively reduced to form racemic Compound VII.

In Variation I of the reaction scheme, the racemic Compound VII is then etherified to racemic Compound VIII which is then reduced to racemic Compond IX. The racemic compound X is obtained from racemic Compound IX by reacting the latter with the phosphonium salts of formula XXIII. Racemic compound X is then esterified to form racemic Compound XI which in turn is oxidized to form racemic Compound XII. Racemic Compound XII is then selectively hydrolyzed to form racemic Compound XIII which is then esterified to form racemic Compound XIV. Racemic Compound XV is obtained from racemic Compound XIV by isomerization employing a divalent palladium catalyst. Racemic Compound XV is converted to racemic Compound XVI by hydrolysis.

In Variation II of the reaction scheme, racemic Compound XVII is obtained by esterification of racemic Compound VII and is then isomerized to form racemic Compound XVIII, a known compound. Racemic Compound XVIII is hydrolyzed to form racemic Compound XIX which is then converted to racemic Compound XX by cyclizing the lactone.

Racemic compound XVI is obtained from racemic Compound XX via racemic intermediates XXI, XXII and XXIV and XXV. Racemic Compound XX is first etherified to form racemic Compound XXI which is then converted to racemic Compound XXII by partial reduction of the lactone group. Racemic Compound XXII is then converted to racemic Compound XXIV by a Wittig reaction employing the phosphonium salts of formula XXIII. A racemic Compound XXIV is then oxidized to form racemic Compound XXV which in turn is hydrolyzed to racemic Compound XVI.

If in the inventive process, optically active Compound I is used as the starting material, optically active intermediates and final product are produced. If the racemic Compound I is employed as the starting material, racemic intermediates and final product are produced. However, if desired, these racemic intermediates may be resolved in order to obtain optically active compounds, the preferred compounds of the present invention. The racemic mixtures may be resolved at the appropriate steps in the process of this invention by methods well known in the art for resolving such racemic mixtures, providing, thereby, the optically pure enantiomers for use in subsequent steps of the reaction scheme.

In accordance with this invention, the optically active starting material of formula I and its racemate can be prepared as follows:

First, a compound of the formula:

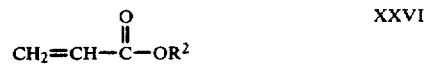

XXVI wherein $R^2$ is hydrogen or a carboxy blocking group convertible to an acid by hydrolysis; is reacted with nitromethane in a conventional manner to produce

XXVII wherein $R^2$ is as above. The compound of formula XXVII is converted to the compound of formula I via the following intermediates:

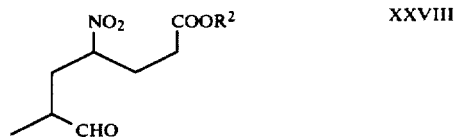

XXVIII wherein $R^2$ is as above and

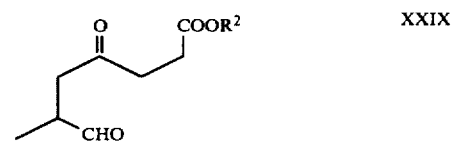

XXIX wherein $R^2$ is as above.

In the first step of this reaction, the compound of formula XXVII is condensed with methacrolein to produce the compound of formula XXVIII. This condensation is carried out in the presence of a base, preferably an alkali metal base such as sodium hydroxide in a lower alkanol solvent. Any conventional lower alkanol solvent can be utilized in carrying out this reaction. In carrying out this reaction, temperatures of from 0° to 30° are generally utilized. The compound of formula XXVIII is converted to the compound of formula XXIX by treating with sodium hydroxide or sodium alkoxide followed by sulphuric acid in the presence of ethyl alcohol, utilizing the Jacobson-Nef reaction. The compound of formula XXIX is converted to the compound of formula I via an aldol condensation. Any of the conditions conventional in aldol condensations can be utilized in cyclizing the compound of formula XXIX to produce the compound of formula I.

The optically active compound of formula I wherein the methyl group is in the alpha position, i.e. a compound of the formula:

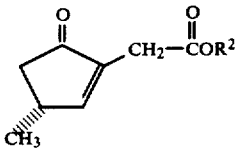

XXX wherein R² is as above can be prepared from S-citronellal via the following intermediates:

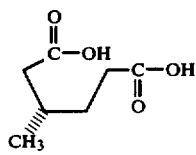

XXXI

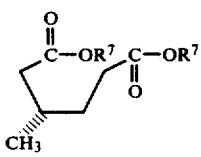

XXXII

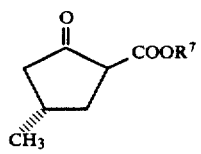

XXXIII

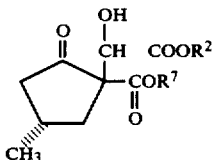

XXXIV

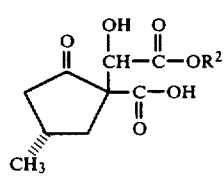

XXXV

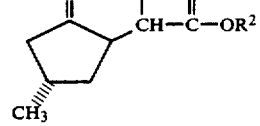

XXXVI

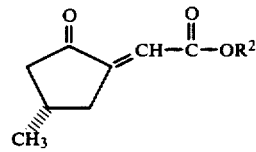

XXXVII wherein R² is as above and R⁷ is t-butyl.

The compound S-citronellal is converted to the compound of formula XXXI via the following two steps. In the first step, citronellal is oxidized with ozone and in the second step, hydrogen peroxide is added to form the compound of formula XXXI. The conditions conventional in oxidizing with ozone and a peroxide oxidizing agent can be utilized in carrying out this reaction. The compound of formula XXXI is converted to the compound of formula XXXII by esterifying to form the t-butyl ester. Any conventional method for converting an organic acid into its t-butyl ester can be utilized in converting the compound of formula XXXI to the compound of formula XXXII. Among the preferred methods is treating the compound of formula XXXI with isobutylene in sulfuric acid. The compound of formula XXXII is converted to the compound of formula XXXIII by Dieckmann cyclization. Any of the conditions conventional in Dieckmann cyclization can be utilized in carrying out this reaction.

In converting the compound of formula XXXIII to the compound of formula XXXIV, the compound of formula XXXIII is reacted with a compound of the formula:

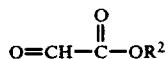

XXXVIII wherein R² is as above.

The compound of formula XXXIII is reacted with the compound of formula XXXVIII to produce the compound of formula XXXVI. It is preferable to use but not necessary to use a secondary or primary amine such as diethylamine, etc. in carrying out this reaction. In the reaction temperature and pressure are not critical. This reaction can be carried out at room temperature and atmospheric pressure. Furthermore, in carrying out this reaction, any conventional secondary or primary amine can be utilized such as the lower alkyl primary or secondary amines. Among the other amines which can be utilized are piperidine, morpholine, etc. On the other hand, this reaction can be carried out in the presence of an organic base such as sodium ethoxide, etc. Furthermore, in carrying out this reaction, any conventional inert organic solvent can be utilized as the reaction medium.

The compound of formula XXXIV is converted to the compound of formula XXXV by hydrolysis with a strong organic acid such as trifluoroacetic acid, propionic acid, etc. In carrying out this reaction, the reaction medium is non-aqueous and any conventional inert organic solvent can be utilized. By this procedure, t-butyl is selectively removed from the compound of formula XXXIV without affecting the other protecting group designated by $R^2$. In carrying out this reaction, temperature and pressure are not critical and generally this reaction is carried out at room temperature.

The compound of formula XXXV is converted to the compond of formula XXXVI by decarboxylating the compound of formula XXXV through conventional means such as by treating with an alkali metal bicarbonate in an aqueous medium at room temperature. On the other hand, if this reaction is carried out at temperature of from 80° C. to 150° C. the compound of formula XXXVII is directly produced from the compound of formula XXXV without going through the intermediate of formula XXXVI. The compound of formula XXXVI can be converted to the compound of formula XXXVII by treating the compound of formula XXXVI with a dehydrating agent. Any conventional dehydrating agent and conditions for dehydration can be utilized in carrying out this reaction. Among the preferred dehydrating agents are the organic acids such as para-toluene sulfonic acid. The compound of formula XXXVII is converted to the optically active compound of formula I i.e. formula XXX by heating in the presence of a basic catalyst such as an organic amine catalyst. Among the amine catalysts are 4-dimethylamino pyridine. However, any of the other conventional amine catalysts can be utilized in carrying out this reaction. This reaction is carried out in an organic solvent. Any conventional organic solvent such as the organic hydrocarbon solvents such as toluene and benzene can be utilized in carrying out this reaction.

The following examples further illustrate the process and the compounds of the invention. In the examples the temperature is in degrees Celsius (°), and room temperature is about 23°. The examples take place under atmospheric pressure unless otherwise stated. In the examples, Triton B means trimethyl benzylammonium hydroxide in methanol; THF means tetrahydrofuran; TLC means thin layer chromatography; Aldrich K Selectride means 1M solution of potassium tris-sec-butylborohydride in THF; "Florisil" is finely divided silica gel; "DIBAL" is diisobutyl aluminum hydride; DMSO is dimethyl sulfoxide; THP is tetrahydropyranyl; and TsOH is para-toluene sulfonic acid. Unless indicated otherwise (for example, by use of other than past verb tense), the examples were carried out as written.

EXAMPLE I

Racemic (1R,2S,3R) 3-Methyl-2-(1RS-1-nitroethyl)-5-oxocyclopentane acetic acid ethyl ester A solution of racemic 3-methyl-5-oxo-1-cyclopentene-1-acetic acid ethyl ester (91.0 g, 0.5 mole) and nitroethane (65 mL, 0.9 mole) in toluene (550 mL) was treated with Triton B in methanol solution (18 mL) and heated to 50° for 2½ hours. The solution was stored at room temperature for 12 hours and washed with 175 mL of 0.3N HCl. After two washes with brine, the organic layer was dried over sodium sulfate and stripped of solvent under reduced pressure. There remained 125.0 g (97.5%) of a yellow oil crude racemic (1R,2S,3R)-3-methyl-2-(1RS-1-nitro-ethyl)-5-oxocyclopentane acetic acid ethyl ester as a mixture of two diastereomers which was used directly in Example II.

An analytical sample of racemic (1R,2S,3R)-3-methyl-2-(1-nitroethyl)-5-oxocyclopentane acetic acid ethyl ester prepared by passing an ether solution through silica gel was seen by TLC and NMR to be a 1:1 mixture of diastereomers.

Anal. Found: C, 56.21; H, 7.50; N, 5.29.

EXAMPLE II

Racemic (3aR,4S,5R,6aS)-4-(1RS-1-nitro-ethyl)hexahydro-5-methyl-2H-cyclopenta[b]furan -2-one A solution of crude (1R,2S,3R)-3-methyl-2-(1-nitroethyl)-5-oxocyclopentane acetic acid ethyl ester (mixture of two diastereomers) (125 g, 0.486 mole) in THF (600 mL) was cooled to (−78°) under argon and treated with a 1M solution of potassium tri-sec-butylborohydride in THF (Aldrich "K-Selectride") (575 mL, 0.575 mole) by dropwise addition with stirring for 1 hour. The solution was stirred for an additional hour and treated with a 10% aqueous solution of sodium hydroxide (275 mL) over a period of 5 minutes. The dry ice/acetone cooling bath was replaced with an ice bath and 30% aqueous hydrogen peroxide (275 mL) was added over a period of 70 minutes while keeping the temperature of the reaction mixture between 0° and 15°. After another 30 minutes the bath was removed and 3N HCl was added (650 mL). This mixture was stirred for 85 minutes and then stripped of most of the solvent under reduced pressure using a 40° bath. The product was extracted twice into ethyl acetate. The combined extract was washed with $NaHCO_3$ solution and with brine, dried over sodium sulfate, and stripped of solvent. The residue of crude racemic (3aR,4S,5R,6aS)-4-(1-nitroethyl)-hexahydro-5-methyl-2H-cyclopenta[b]furan-2-one was a green oil weighing 91.5 g (88.3%).

EXAMPLE III

Racemic (3aR,4S,5R,6aS)-4-acetylhexahydro-5-methyl-2H-cyclopenta-[b]furan-2-one

A solution of sodium hydroxide (22 g, 0.55 mole) in methanol (275 mL) was cooled to 0° and added all at once to a cold (0°) solution of crude, racemic (3aR,4S,5R,6aS)-4-(1-nitroethyl)hexahydro-5-methyl-2H-cyclopenta[b]furan-2-one (91.5 g, 0.43 mole) in methanol (350 mL). The resulting solution was stirred without further cooling for 1½ hours during which time a solution of concentrated sulfuric acid (65 mL, 1.22 mole) in methanol (350 mL) was prepared by slow addition of the acid to the methanol while stirring and cooling in a dry ice/acetone bath. Both solutions were chilled to (−35°) and the nitronate anion solution as added all at once to the acid solution. This mixture was kept for 1½ hours during which the color changed from yellow to a pale blue-green. Approximately 500 mL of methanol was stripped off under reduced pressure using a 35° bath and a solution of acetic acid (50 mL) in water (300 mL) was added. Stripping was continued for 1¼ hours (40° bath) during which the remaining solvent was removed. The product was extracted with ethyl acetate. The extract was washed with $NaHCO_3$ solution and with brine, dried over sodium sulfate, and stripped of solvent. The racemic (3aR,4S,5R,6aS)-4-acetylhexahydro-5-methyl-2H-cyclopenta[b]furan-2-one thus obtained was 70.8 g (90.5%) of amber-colored oil. The yield based on racemic 3-methyl-5-oxo-1-cyclopentene-1-acetic acid ethyl ester was 77.8%. A sample for analysis was vacuum distilled giving a colorless liquid. Anal. Found: C, 65.78; H, 7.91.

If desired, racemic (3aR,4S,5R,6aS)-4-(1,1-dimethoxyethyl)-hexahydro-5-methyl-2H-cyclopenta[b]furan-2-one can be isolated at this point by evaporating the methanol, quenching the reaction mixture with cold aqueous, sodium carbonate solution and extracting the product with ethyl acetate.

EXAMPLE IV

Racemic (3aR,4S,5R,6aS)-[S*,R*(E)]-4-(4,4-Dimethyl-1-oxo-2-octenyl)hexahydro-5-methyl-2H-cyclopenta[b]furan-2-one A solution of potassium (7.8 g, 0.2 mole) in t-butyl alcohol (500 mL) was prepared and to it the crude, racemic (3aR,4S,5R,6aS)-4-acetylhexahydro-5-methyl-2H-cyclopenta[b]furan-2-one (21.3 g, 0.117 mole) was added followed by the 2,2-dimethylhexanal (16.4 g, 0.128 mole), both at room temperature. The resulting solution was stirred under argon for 1½ hours, after which the reaction was ascertained by TLC to be complete. Concentrated HCl (40 mL) was then added and the solvent was stripped off under reduced pressure using a 40° bath. The residue was partitioned between water and ether and the ether layer was washed with $NaHCO_3$ solution and with brine. After drying over sodium sulfate, the solvent was stripped off leaving a yellow, oily residue of crude racemic (3aR,4S,5R,6aS)-[S*,R*(E)]-rac-4-(4,4-Dimethyl-1-oxo-2-octenyl)hexahydro-5-methyl-2H-cyclopenta[b]furan-2-one. This material changed to a viscous, semicrystalline mass when stored in the cold. The yield was 28.6 g (84%).

An analytical sample was crystallized from hexane giveing colorless crystals with mp 28°-31°. Anal. Found: C, 73.66; H, 9.82.

EXAMPLE V

Racemic [3aR-[3a alpha,4alpha-(1S*,2E),5beta,6a alpha]]-4-[1-(hydroxy)-4,4-dimethyl-2-octenyl]hexahydro-5-methyl-2H-cyclopenta[b]furan-2-one The crude racemic (3aR,4S,5R,6aS)-[S*,R*-(E)]-rac-4-(4,4-Dimethyl-1-oxo-2-octenyl)hexahydro-5-methyl-2H-cyclopenta[b]furan-2-one (10.0 g, 0.0342 mole) in methanol (150 mL) solution was cooled to 0° and treated with sodium borohydride (1.0 g, 0.0264 mole). After stirring for 1 hour at 0°, 3N HCl (15 mL) was added dropwise. The methanol was stripped off under reduced pressure using a 40° bath and the residue was partitioned between water and ether. The ether layer was was washed with $NaHCO_3$ solution and with brine, dried over sodium sulfate and stripped of solvent. The residue of crude, racemic [3aR-[3a alpha,4alpha-(1S*,2E),5beta, 6a alpha]]-4-[1-(hydroxy)-4,4-dimethyl-2-octenyl]hexahydro-5-methyl-2H-cyclopenta[b]furan-2-one was viscous amber oil weighing 10.26 g (100%).

EXAMPLE VI

Racemic [3aR-[3a alpha,4alpha-(1S*,2E),5beta,6a alpha]]-4-[1-(hydroxy)-4,4-dimethyl-2-octenyl]hexahydro-5-methyl-2H-cyclopenta[b]furan-2-one The crude racemic (3aR,4S,5R,6aS)-[S*,R*(E)]-rac-4-(4,4-Dimethyl-1-oxo-2-octenyl)hexahydro-5-methyl-2H-cyclopenta[b]furan-2-one (12.9 g, 0.044 mole) in THF (60 mL) solution was cooled to −77° and treated dropwise with a 1M solution of potassium tri-sec-butylborohydride in THF (Aldrich "K-Selectride") (56 mL, 0.056 mole). Stirring at −77° was continued for 1½ hours after the addition was completed. An aqueous solution of 10% NaOH (30 mL) was then added and the mixture allowed to warm to −20°. Aqueous 30% $H_2O_2$ (30 mL) was then added dropwise while keeping the temperature in the −5° to +5° range. After 1 hour, the cooling bath was removed and 3N HCL (90 mL) was added. Following 2 hours more of stirring, most of the solvent was stripped off and the product was taken up in ethyl acetate (200 mL). This solution was washed with aqueous $NaHCO_3$, brine, and dried over $Na_2SO_4$. The volume was reduced to 100 mL by evaporation and this solution of crude [3aR-[3a alpha;4alpha-(1S*,2E),-5beta,6a alpha]]-4-[1-(hydroxy)-4,4-dimethyl-2-octenyl]hexahydro-5-methyl-2H-cyclopenta[b]furan-2-one was used directly in Example VII.

EXAMPLE VII

Racemic [3aR-[3a alpha,4alpha(1S*,2E),5beta,6a alpha]]-4-[1-(Acetyloxy)-4,4-dimethyl-2-octenyl]-hexahydro-5-methyl-2H-cyclopenta-[b]furan-2-one The solution of crude racemic [3aR-[3a alpha,-4alpha(1S*,2E),5beta,6a alpha]]-4-[1-(Hydroxy)-4,4-dimethyl-2-octenyl]hexahydro-5-methyl-2H-cyclopenta[b]furan-2-one from Example VI was treated with acetic anhydride (15 mL) and 4-dimethylaminopyridine (200 mg). The resulting solution was heated to reflux for 45 minutes, cooled, washed with water, aqueous, $NaHCO_3$, and brine. After drying over $Na_2SO_4$ and stripping the solvent, 18.2 g of light yellow oil remained.

This crude acetate was dissolved in hexane (30 mL) and stored in a cold refrigerator for 3 days. A total of 8.55 g (58%) of racemic 3aR-[3a alpha,4alpha[1S*,2E),-5beta, 6a alpha]]-4-[1-(acetyloxy)-4,4-dimethyl-2-octenyl]hexahydro-5-methyl-2H-cyclopenta[b]furan-2-one colorless crystals, mp 63°-65° was collected in 3 crops.

EXAMPLE VIII

Racemic [3aR-[3a alpha,4alpha(1E,3R*),5beta,6a alpha]]-4-[3-(Acetyloxy)-4,4-dimethyl-1-octenyl]hexahydro-5-methyl-2H-cyclopenta[b]furan-2-one A soluttion of the crystalline racemic [3aR-[3a alpha, 4 alpha-(1S*,2E),5beta,6a alpha]]-4-[1-(acetyloxy)-4,4-dimethyl-2-octenyl]hexahydro-5-methyl-2H-cyclopenta[b]furan-2-one from Example VII (8.40 g) in THF (250 mL) was treated with bis-(acetonitrile)palladium (II) chloride (265 mg. 4 mole %) and stirred at 21° under argon for 20 hours. The solution was then concentrated to a volume of ~150 mL and diluted with an equal volume of hexane. It was then passed through a plug of silica gel to remove the catalyst. The silica gel was washed with hexane (100 mL) and the combined filtrate and washing was stripped of solvent. The residue was a light yellow oil weighing 8.01 g and consisting of an approximately 40/60 mixture of racemic [3aR-[3a alpha,4alpha-(1S*,2E),5beta,6a alpha]]-4-[1-(acetyloxy)-4,4-dimethyl-2-octenyl]-hexahydro-5-methyl-2H-cyclopenta[b]furan-2-one and racemic [3aR-[3a alpha,4alpha(1E,3R*),5beta,6a alpha]]-4-[3-(acetyloxy)-4,4-dimethyl-1-octenyl]hexahydro-5-methyl-2H-cyclopenta[b]furan-2-one.

EXAMPLE IX

Racemic [1R-[1 alpha, 2 beta (1E,3R*),3 alpha, 5 alpha]]-5-Hydroxy-2-(3-hydroxy-4,4-dimethyl-1-octenyl)-3-methylcyclopentaneacetic acid The hydrolysis was carried out in a two phase system consisting of 8.01 g of the mixture of racemic [3aR-[3a alpha,4alpha(1S*,2E),5beta,6a alpha]]-4-[1-(acetyloxy)-4,4-dimethyl-2-octenyl]hexahydro-5-methyl-2H-cyclopenta[b]furan-2-one and racemic [3aR-[3a alpha,-4alpha(1E,3R*), 5beta,6a alpha]]-4-[3-(acetyloxy)-4,4-dimethyl-1-octenyl]hexahydro-5-methyl-2H-cyclopenta[b]furan-2-one in toluene (40 mL) and sodium hydroxide (2.89 g) in dionized water (72 mL). This mixture was stirred at 60° overnight, then cooled to 0°-3° and diluted with more deionized water (72 mL). The mixture was acidified by adding a solution of $H_3PO_4$ (8.67 g) in deionized water (43 mL) gradually (during 30 minutes). A seed crystal of [1R-[1 alpha, 2 beta (1E,3R*),3 alpha, 5 alpha]]-5-hydroxy-2-(3-hydroxy-4,4-dimethyl-1-octenyl)-3-methyl-cyclopentane acetic acid was added to induce crystallization. After stirring at 0°-3° for an additional hour, the product was collected by filtration, washed with water and toluene and then dried to give 4.37 g (58.8% based on weight of the racemic starting material mixture) of [1R-[1 alpha, 2 beta(1E,3R*),3 alpha, 5 alpha]]-5-hydroxy-2-(3-hydroxy-4,4-dimethyl-1-octenyl)-3-methylcyclopentane acetic acid as colorless crystals, mp 106°-8°.

The toluene layer of the filtrate was combined with two (2×50 mL) toluene extracts of the aqueous layer, washed with water (150 mL), dried over sodium sulfate and evaporated to give 2.55 g (36.4%) of the racemic [3aR-[3a alpha,4alpha(1S*,2E),-5beta,6a alpha]]-4-(1-(hydroxy)-4,4-dimethyl-2-octenyl]-hexahydro-5-methyl-2H-cyclopenta [b]furan-2-one. This material was recycled to the [3aR-[3a alpha,4alpha(1S*,2E),5beta,-6aalpha]]-4-(1-(acetyloxy)-4,4-dimethyl-2-octenyl]hexahydro-5-methyl-2H-cyclopenta[b]furan-2-one as described in Example VII. 1.90 g of pure crystalline [3aR-[3a alpha,4alpha(1S*,2E), 5beta,6a alpha]]-4-(1-(acetyloxy)-4,4-dimethyl-2-octenyl]hexahydro-5-methyl-2H-cyclopenta[b]furan-2-one was obtained.

EXAMPLE X

Racemic (3aR,4R,5R,6aS,1'E,3'R)-3,3a,4,5,6,6a-hexahydro-4-(4',4'-dimethyl-3'-hydroxy-1-octenyl)-5-methyl-2H-cyclopenta[b]furan-2-one The 4.37 of racemic [1R-[1alpha,2 beta(1E,3R*),3 alpha, 5 alpha]]-5-hydroxy-2-(3-hydroxy-4,4-dimethyl-1-octenyl)-3-methylcyclopentane acetic acid from Example IX was stirred overnight at room temperature in acetic acid (21.5 mL). The solution was then partitioned between toluene (43 mL) and water (86 mL). Two toluene (2×22 mL) extracts of the aqueous layer were combined with the toluene layer, washed once with water (50 mL), twice with 5% aqueous $NaHCO_3$ solution (2×50 mL), once more with water (50 mL), dried over $Na_2SO_4$, and evaporated. The residue was freed of solvent under high vacuum giving 4.06 g (98.5%) of racemic (3aR,4R,5R,6aS,1'E,3'R)-3,3a,4,5,6,6a-hexahydro-4-(4',4'-dimethyl-3'-hydroxy-1-octenyl)-5-methyl-2H-cyclopenta[b]furan-2-one as a colorless oil. The product was ascertained to be pure by TLC.

EXAMPLE XI

Optically Active (1R,2S,3R)-3-methyl-2-(1-nitroethyl)-5-oxocyclopentane acetic acid ethyl ester A solution of optically active (R)-3-methyl-5-oxo-1-cyclopentene-1-acetic acid ethyl ester (9.9 g, 0.0543 mole) and nitroethane (6.6 mL) in toluene (60 mL) was treated with Triton B solution (2 mL) and processed as described in Example I.

The product obtained, optically active (1R,2S,3R)-3-methyl-2-(1-nitroethyl)-5-oxocyclopentane acetic acid ethyl ester, was a pale yellow oil weighing 13.78 g (98%). This was used directly in Example XII.

EXAMPLE XII

Optically Active (3aR,4S,-5R,6aS)-4-(1-nitroethyl)hexahydro-5-methyl-2H-cyclopenta[b]furan-2-one The crude optically active (1R,2S,3R)-3-methyl-2-(1-nitroethyl)-5-oxocyclopentane acetic acid ethyl ester (13.7 g) in THF (65 mL) was reduced with K-Selectride solution (61.5 mL) as described in Example II, and worked up as described in Example II, to give 10.0 g (88%) of crude, optically active 3(3aR,4S,5R,6aS)-4-(1-nitroethyl)-hexahydro-5-methyl-2H-cyclopenta[b]furan-2-one as a green oil.

EXAMPLE XIII

Optically Active (3aR,4S,-5R,6aS)-4-acetylhexahydro-5-methyl-2H-cyclopenta[b]furan-2-one The nitronate anion solution was prepared with sodium methoxide.

Sodium (1.3 g) was dissolved in methanol (30 mL) and the solution added at 0° to a methanol (40 mL) solution of the crude, optically active (3aR,4S,5R,6aS)-4-(1-nitroethyl)hexahydro-5-methyl-2H-cyclopenta[b]furan-2-one (10.0 g). This nitronate anion solution was added, 30 minutes later and at −30°, to a cold (−30°) solution of concentrated sulfuric acid (6 mL) in methanol (40 mL). The resulting mixture was processed as in Example III, including hydrolysis with acetic acid (8 mL) in water (30 mL) while stripping, to give 8.47 g (99%) of the crude, optically active (3aR,4S,-5R,6aS)-4-acetylhexahydro-5-methyl-2H-cyclopenta[b]furan-2-one as a yellow oil. This material was used directly in Example XIV.

EXAMPLE XIV

Optically Active (3aR,4S,5R,6aS)-[S*,R*(E)]-4-(4,4-Dimethyl-1-oxo-2-octenyl)hexahydro-5-methyl-2H-cyclopenta[b]furan-2-one A solution of sodium (2.2 g, 0.0955 mole) in ethanol (100 mL) was prepared and cooled to 0°. To it was added under argon a solution of the crude, optically active (3aR,4S,5R,6aS)-4-acetylhexahydro-5-methyl-2H-cyclopenta[b]furan-2-one (8.4 g, 0.0462 mole) in ethanol (20 mL), followed by the 2,2-dimethyl hexanal (7.7 g, 0.060 mole). The resulting solution was heated to 55° under argon for 1½ hours, during which the color changed from amber to dark brown. Concentrated HCl (10 mL) was added and the reaction was worked up as described in Example IV to give 11.78 g of crude product as a brown oil. This was dissolved in hexane (100 mL), stirred with "Florisil", filtered, combined with a hexane (50 mL) washing of the "Florisil", and evaporated to give 11.1 g (82.2%) of (3aR,4S,-5R,6aS)-[S*,R*(E)]-4-(4,4-dimethyl-1-oxo-2-octenyl)hexahydro-5-methyl-2H-cyclopenta[b]furan-2-one as an amber colored oil.

EXAMPLE XV

Optically Active [3aR-[3a alpha,4alpha(1S*,2E),5beta,6a alpha]]4-[1-(hydroxy)-4,4-dimethyl-2-octenyl]hexahydro-5-methyl-2-H-cyclopenta[b]furan-2-one The crude, optically active (3aR,4S,-5R,6aS)-[S*,R*(E)]-4-(4,4-dimethyl-1-oxo-2-octenyl)hexahydro-5-methyl-2H-cyclopenta[b]furan-2-one (11.1 g) was reduced with sodium borohydride (1.1 g) as described in Example V. After workup 10.45 g (93%) of optically active [3aR-[3aalpha,4alpha(1S*,2E),5beta,6aalpha]]-4-[1-(hydroxy)-4,4-dimethyl)-2-octenyl]hexahydro-5-methyl-2H-cyclopenta[b]furan-2-one was obtained as a viscous, amber colored oil. The product gave a single spot on TLC and was used as is in Examples XVI through XXIV of the synthesis.

EXAMPLE XVI

Optically Active [3aR-[3a alpha,4alpha(1S*,2E),5beta,6a alpha]]-4-[1-(2-Tetrahydropyranyloxy)-4,4-dimethyl-2-octenyl]hexahydro-5-methyl-2H-cyclopenta[b]furan-2-ol A solution of the optically active [3aR-[3a alpha,4alpha(1S*,2E),5beta,6a alpha]]-4-[1-(hydroxy)-4,4-dimethyl-1-octenyl]hexahydro-5-methyl-2H-cyclopenta[b]furan-2-one (10.4 g) in toluene (100 mL) was treated with dihydropyran (6.0 mL) and p-TsOH (30 mg). After 2 hours at room temperature, the reaction was complete.

At this point, crude optically active [3aR-[3a alpha,4 alpha (1S*,2E),5 beta, 6a alpha] can be isolated, if desired by evaporating the toluene and excess dihydropyran under reduced pressure.

However this solution was then chilled to (−78°) in a dry ice/acetone bath and treated, while stirring, with freshly opened 25% solution of diisobutylaluminum hydride ("DIBAL-H") (34 mL) by dropwise addition over a period of 15 min.

After another 15 min, the reaction was quenched by pouring it into brine (100 mL). The pH was adjusted to 3 by adding 3N HCl (ca. 60 mL) and the organic layer was separated. After washing with NaHCO₃ solution and with brine, the organic layer was dried over sodium sulfate and stripped of solvent; finally under high vacuum. The residue of crude optically active [3aR-[3a alpha, 4alpha(1S*,2E),5beta,6a alpha]]-4-[1-(2-Tetrahydropyranyloxy)-4,4-dimethyl-2-octenyl]hexahydro-5-methyl-2H-cyclopenta[b]furan-2-ol was a yellow oil weighing 13.8 g (∼100%).

EXAMPLE XVII

Optically Active (5Z,11alpha,13S,14E)-13-2-tetrahydropyranyloxy)-11,16,16-Trimethyl-9-hydroxyprosta-5,14-dien-1-oic acid (4-carboxybutyl)triphenylphosphonium bromide (40.8 g, 0.0921 mole) and potassium t-butoxide (24.0 g, 0.214 mole) were combined with reagent grade tetrahydrofuran (130 mL) in a flask and stirred under argon for 30 minutes. A solution of the optically active [3aR-[3aalpha,4alpha(1S*,2E),5beta,6aalpha]]-4-[1-(2-tetrahydropyranyloxy)-4,4-dimethyl-2-octenyl]hexahydro-5-methyl-2H-cyclopenta[b]-furan-2-ol (13.8 g, 0.0353 mole) in tetrahydrofuran (100 ml) was added dropwise. The resulting mixture was stirred at room temperature for 1½ hours and then quenched by dropwise addition of acetic acid (5.4 mL). Water (100 mL) was then added and most of the tetrahydrofuran was removed under reduced pressure using a 40° bath. Methanol (100 mL) was added to the residue which was then extracted twice with 100 mL hexane each time. The hexane layers were combined and back extracted with a methanol (100 mL)/aqueous NaHCO₃ (100 mL) mixture and discarded. The aqueous methanol layers were acidified with 6N HCl and extracted with hexane (3×100 mL). The combined hexane extracts were washed with 1:1 water/methanol (50 mL) and with brine, dried over sodium sufate and stripped of solvent to given 11.7 g (71%) of crude optically active (5Z,11alpha,13S,14E)-13-(2-tetrahydropyranyloxy)-11,16,16-trimethyl-9-hydroxyprosta-5,14-dien-1-oic acid as a yellow oil.

EXAMPLE XVIII

Optically Active (5Z,11alpha,13S,14E)-13-(2-tetrahydropyranyloxy)-11,16,16-Trimethyl-9-hydroxyprosta-5,14-dien-1-oic acid methyl ester The crude optically active (5Z,11alpha,13S,14E)-13-(2-tetrahydropyranyloxy)-11,16,16-trimethyl-9-hydroxyprosta-5,14-dien-1-oic acid (11.7 g) in dimethylacetamide (60 mL) solution was treated with sodium bicarbonate (14.0 g) and methyl iodide (13.0 mL). The mixture was stirred under argon at room temperature while protected from direct light for 25 hours. The mixture was then poured into water (200 mL) and the product was extracted three times using 100 mL hexane each time. The combined extracts were washed with water, aqueous methanol (1:1), and brine. After drying over sodium sulfate and evaporation of solvent, 11.1 g (92%) of crude optically active (5Z,11alpha,13S,14E)-13-(2-tetrahydro-pyranyloxy)-11,16,16-trimethyl-9-hydroxyprosta-5,14-dien-1-oic acid methyl ester was obtained as a yellow oil.

EXAMPLE XIX

Optically Active (5Z,11alpha,13S,14E)-13-(12-tetrahydropyranyloxy)-11,16,16-Trimethyl-9-oxoprosta-5,14-dien-1-oic acid methyl ester A DMSO (60 mL) solution of the crude optically active (5Z,11alpha,13S,14E)-13-(2-tetrahydropyranyloxy)-11,16,16-trimethyl-9-hydroxyprosta-5,14-dien-1-oic acid methyl ester (11.1 g) was treated with triethylamine (22 mL) and then dropwise with a DMSO (60 mL) solution of sulfur trioxide pyridine complex (11.1 g) during 30 minutes while stirring. After 3½ hours, the reaction mixture was poured into a slush of ice and brine (600 mL) and extracted with hexane (3×150 mL). The combined extracts were washed with 2N HCL, water, NaHCO₃ solution, and brine, then dried over sodium sulfate and stripped of solvent. The crude optically active (5Z,11alpha,13S,14E)-13-(2-tetrahydropyranyloxy)-11,16,16-Trimethyl-9-oxoprosta-5,14-dien-1-oic acid methyl ester was obtained as a yellow oil weighing 10.55 g (95.4%).

EXAMPLE XX

Optically Active
(5Z,11alpha,13S,14E)-13-(Hydroxy)-11,16,16-Trimethyl-9-oxoprosta-5,14-dien-1-oic acid methyl ester The crude optically active (5Z,11alpha,13S,14E)-13-(2-tetrahydropyranyloxy)-11,16,16-Tri-methyl-9-oxoprosta-5,14-dien-1-oic acid methyl ester (10.55 g) in methanol (100 mL) solution was treated with pyridinium p-toluenesulfonate (1.0 g) and stirred under argon at 40° for 24 hours. After cooling it, the solution was poured into brine (500 mL) and the product was extracted three times with hexane (150 mL each time). The combined extract was dried over sodium sulfate and stripped of solvent to give 9.5 g (~100%) of optically active (5Z,11alpha,13S,14E)-13-hydroxy-11,16,16-trimethyl-9-oxoprosta-5,14-dien-1-oic acid methyl ester as a yellow oil.

EXAMPLE XXI

Optically Active
(5Z,11alpha,13S,14E)-13-(Acetyloxy)-11,16,16-trimethyl-9-oxoprosta-5,14-dien-1-oic acid methyl ester A solution of the crude optically active (5Z,11alpha,13S,14E)-13-(hydroxy)-11,16,16-trimethyl-9-oxoprosta-5,14-dien-1-oic acid methyl ester (9.2 g) in methylene chloride (100 mL) was treated with pyridine (5.5 mL) and 4-dimethylaminopyridine (0.5 g), cooled to 0°, and treated with acetic anhydride (3.4 mL). The resulting mixture was stirred overnight at room temperature and then washed with 2N HCL, water, NaHCO3 solution, and brine (75 mL of each). After drying over sodium sulfate, the solvent was stripped off leaving 9.7 g (~100%) of crude optically active (5Z,11alpha,13S,14E)-13-(acetyloxy)-11,16,16-trimethyl-9-oxoprosta-5,14-dien-1-oic acid methyl ester as a yellow oil. This material was used as is in Example XXII.

EXAMPLE XXII

Optically Active
(5Z,11alpha,,13E,15R)-15-acetyloxy-11,16,16-trimethyl-9-oxoprosta-5,13-dien-1-oic acid methyl ester A solution of the crude optically active (5Z,11alpha,13S,14E)-13-(acetyloxy)-11,16,16-trimethyl-9-oxoprosta-5,14-dien-1-oic acid methyl ester (9.4 g, 0.0217 mole) in 1,2-dimethoxyethane (300 mL) was treated with bis-(acetonitrile) palladium (II) chloride (200 mg). The solution was stirred under argon at 65° for a total of 40 hours. Three additional 200 mg portions of catalyst were added at 5-10 hours intervals for a total of 800 mg (0.00308 mole) of catalyst. The volume of the solution was reduced by ½ by evaporation under reduced pressure and an equal volume of hexane (~150 mL) was added. This solution was filtered through a plug of silica gel to remove the catalyst and polar by-products. The silica gel was washed with 1:1 hexane/ethyl acetate (500 mL). Evaporation of the combined filtrate and washing gave 8.4 g of yellow oil. This material was again treated with the palladium catalyst (200 mg) in 1,2-dimethoxyethane (200 mL) solution at 60° under argon for 6 hours and worked up as above. The resulting crude isomerization product consisted of 8.1 g of yellow oil.

The isolation of optically active (5Z,11alpha,13E,15R)-15-acetyloxy-11,16,16-trimethyl-9-oxoprosta-5,13-dien-1-oic acid methyl ester from the isomerization mixture was accomplished with a Waters 500 Prep. HPLC using four Silica cartridges and 9% ethyl acetate in hexane at a flow rate of 250 mL/min. The 2.85 g of optically active (5Z,11alpha,13E,15R)-15-acetyloxy-11,16,16-trimethyl-9-oxoprosta-5,13-dien-1-oic acid methyl ester obtained was combined with 0.42 g obtained by reprocessing the recovered optically active (5Z,11alpha,13S,14E)-13-(acetyloxy)-11,16,-16-trimethyl-9-oxoprosta-5,14-dien-1-oic acid methyl ester for a total yield of 3.27 g (35% based on crude optically active (5Z,11alpha,13S,14E)-13-(acetyloxy)-11,-16,16-trimethyl-9-oxoprosta-5,14-dien-1-oica cid methyl ester.

EXAMPLE XXIII

Optically Active
(5Z,11alpha,13E,15R)-15-hydroxy-11,16,16-trimethyl-9-oxoprosta-5,13-dien-1-oic acid A solution of optically active (5Z,11alpha,13E,15R)-15-acetyloxy-11,16,16-trimethyl-9-oxoprosta-5,13-dien-1-oic acid methyl ester (3.2 g) in methanol (32 mL) was treated with 4N NaOH (6.4 mL) and stirred under argon for 20 hours. The solution was acidified with 2N HCl and the product recovered by ethyl acetate extraction. There was thus obtained 3.0 g (~100%) of crude optically active (5Z,11alpha,13E,15R)-15-hydroxy-11,16,16-trimethyl-9-oxoprosta-5,13-dien-1-oic acid as a yellow oil.

EXAMPLE XXIV

Optically Active
[3aR-[3aalpha,4alpha(1S*,2E),5beta,6a alpha-]]-4-[1-(acetyloxy)-4,4-dimethyl-2-octenyl]hexahydro-5-methyl-2H-cyclopenta[b]furan-2-one Following the procedure of example VII, 48.9 g, of crude, optically active [3aR-[3a alpha,4alpha(1S*,2E), 5beta,6a alpha-]]-4-[1-(hydroxy)-4,4-dimethyl-2-octenyl]hexahydro-5-methyl-2H-cyclopenta[b]furan-2-one was acetylated with 60 ml of acetic anhydride and 0.5 g of 4-dimethylaminopyridine in 400 ml of ethyl acetate. The product was crystallized from 60 ml of hexane giving 30.05 g of optically active [3aR-[3aalpha,-4alpha(1S*,2E),5beta, 6a alpha-]]-4-[1-(acetyloxy)-4,4-dimethyl-2-octenyl]hexahydro-5-methyl-2H-cyclopenta[b]furan-2-one in colorless crystals with mp 83°-83.5°.

EXAMPLE XXV

Optically Active
[3aR-[3aalpha,4alpha(1E,3R*),5beta,6a alpha]]-4-[3-(acetyloxy)-4,4-dimethyl-1-octenyl]hexahydro-5-methyl-2H-cyclopenta[b]furan-2-one Following the procedures of Example VIII, 30.0 g of crystalline optically active [3aR-[3aalpha,4alpha(1S*,2E), 5beta,6a-alpha-]]-4-[1-(acetyloxy)-4,4-dimethyl-2-octenyl]hexahydro-5-methyl-2H-cyclopenta[b]furan-2-one was isomerized by treating it in THF solution (850 mL) with 0.925 g of bis-(acetonitrile)palladium (II) chloride. Part of the starting material crystallized from the product mixture and was recovered by filtration giving 5.83 g of colorless crystals. Evaporation of the filtrate afforded 23.40 g of a mixture of the two isomers, the major component being optically active [3aR-[3aalpha,4alpha(1E,3R*),5beta,6a alpha]]-4-[3-(acetyloxy)-4,4-dimethyl-1-octenyl]hexahydro-5methyl-2H-cyclopenta[b]furan-2-one.

EXAMPLE XXVI

Optically Active [1R-[1alpha,2beta(1E,3R*),3alpha,5alpha]]-5-hydroxy-2-(3-hydroxy-4,4-dimethyl-1-octenyl)-3-methylcyclopentane acetic acid Following the procedure of Example IX, 23.33 g of crude optically active [3aR-[3a alpha,4alpha(1E,3R*),-5beta, 6a alpha]]-4-[3-(acetyloxy)-4,4-dimethyl-1-octenyl]hexahydro-5-methyl-2H-cyclopenta[b]furan-2-one obtained from the isomerization step was hydrolyzed in a mixture consisting of 150 mL of toluene and 265 mL of 1N aqueous sodium hydroxide solution. The product was precipitated from this mixture by gradual acidification at 0°–3° with a solution of 32 g of phosphoric acid in 130 mL of water. The product was collected by filtration, washed with water and with toluene, and dried to give 14.0 g of optically active [1R-[1alpha,2beta(1E,3R*),3alpha,5alpha]]-5-hydroxy-2-(3-hydroxy-4,4-dimethyl-1-octenyl)-3-methylcyclopentane acetic acid. For further purification the product was again dissolved in a mixture of toluene and aqueous sodium hydroxide and then reprecipitated with dilute phosphoric acid to give, after washing and drying, 13.3 g of crystalline product with mp. 99.9°–102°.

EXAMPLE XXVII

Optically Active 3aR,4R,5R,6aS,1'E,3'R)-3,3a,4,5,6,6a-hexahydro-4-(4',4'-dimethyl-3'-hydroxy-1-octenyl)-5-methyl-2H-cyclopenta[b]furan-2-one Following the procedure of Example X, 13.2 g of purified optically active [1R-[1alpha,2beta(1E,3R*),3alpha, 5alpha]]-5-hydroxy-2-(3-hydroxy-4,4-dimethyl-1-octenyl)-3-methylcyclopentane acetic acid was lactonized in 65 ml of acetic acid. The product, 3aR,4R,5R-,6aS,1'E,3'R)-3,3a,4,5,6,6a-hexahydro-4-(4',4'-dimethyl-3'-hydroxy-1-octenyl)-5-methyl-2H-cyclopenta[b]furan-2-one, was recovered from the reaction mixture after dilution with 120 mL of water by solvent extraction using 180 mL of a 2:1 hexane/ethyl acetate mixture. The product was obtained as a colorless oil weighing 12.32 g.

We claim:

1. An optically active compound of the formula:

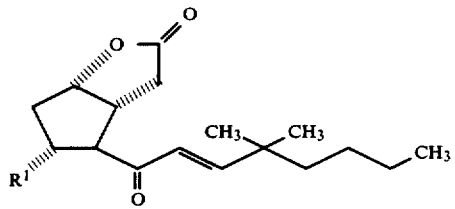

wherein $R^1$ is hydrogen or lower alkyl; and its racemate.

2. The compound of claim 1 wherein $R^1$ is methyl.
3. An optically active compound of the formula:

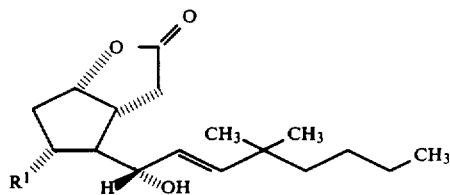

wherein $R^1$ is hydrogen or lower alkyl; and its racemate.

4. The compound of claim 3, wherein $R^1$ is methyl.
5. An optically active compound of the formula:

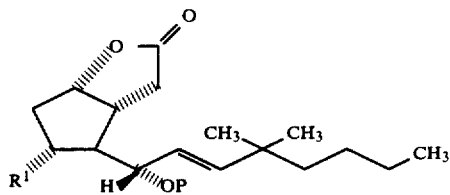

wherein $R^1$ is hydrogen or lower alkyl and P is a hydrolyzable ether protecting group; and its racemate.

6. The compound of claim 5 wherein $R^1$ is methyl and P is an alkyl silyl; 2-methoxy-2-propyl; or tetrahydropyranyl.
7. The compound of claim 5 wherein $R^1$ is methyl and P is tetrahydropyranyl.
8. An optically active compound of the formula:

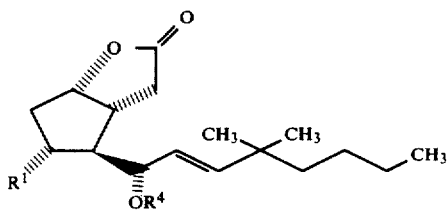

wherein $R^1$ is hydrogen or lower alkyl, and $R^4$ is acyl; and its racemate.

9. The compound of claim 8, wherein $R^1$ is methyl and $R^4$ is acetyl.

* * * * *